US00PP24791P3

(12) United States Plant Patent
Ui et al.

(10) Patent No.: US PP24,791 P3
(45) Date of Patent: Aug. 19, 2014

(54) ***PETUNIA-CALIBRACHOA* HYBRID PLANT NAMED 'SAKPXC011'**

(50) Latin Name: ***Petunia-Calibrachoa* intergeneric hybrid**
Varietal Denomination: SAKPXC011

(71) Applicant: Sakata Seed Corporation, Yokohama (JP)

(72) Inventors: Akinobu Ui, Iwata (JP); Shin Ishikawa, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 119 days.

(21) Appl. No.: 13/694,535

(22) Filed: Dec. 11, 2012

(65) Prior Publication Data
US 2014/0165249 P1 Jun. 12, 2014

(51) Int. Cl.
*A01H 5/00* (2006.01)

(52) U.S. Cl.
USPC ..... Plt./356.11

(58) Field of Classification Search
CPC ..... A01H 5/00; A01H 5/02
USPC ..... Plt./356.11
See application file for complete search history.

*Primary Examiner* — Susan McCormick Ewoldt
(74) *Attorney, Agent, or Firm* — James M. Weatherly; Cochran Freund & Young LLC

(57) ABSTRACT

A new *Petunia-Calibrachoa* hybrid plant particularly distinguished by having a purplish-rose flower color and semi-creeping growth habit is disclosed.

1 Drawing Sheet

Genus and species: *Petunia-Calibrachoa* intergeneric hybrid.

Variety denomination: 'SAKPXC011'.

BACKGROUND OF THE NEW PLANT

The present invention comprises of a new and distinct cultivar of *Petunia-Calibrachoa* (Petchoa) referred to by the variety name 'SAKPXC011'. *Petunia-Calibrachoa* variety 'SAKPXC011' originated from a hybridization in Kakegawa, Japan in December 2006. The male parent was a commercial patented hybrid *Calibrachoa* line named 'SAKCAL093' (U.S. Plant Pat. No. 20,490), which has a burgundy flower color and a creeping plant habit. The female parent was a proprietary hybrid *Petunia* line named 'AM6-106A' (unpatented), which had a rose flower color and a mounding plant habit.

In December 2006, an $F_1$ generation from the initial hybridization was grown and approximately 50 seeds were obtained. In February 2007, 120 seeds were sown and the plants were cultivated in a greenhouse and only one plant survived and bloomed. Segregation in the $F_1$ generation resulted in the one plant having a purplish-rose flower color and a semi-creeping plant growth habit. In May 2007, the plant was selected that exhibited the purplish-rose flower color and semi-creeping plant growth habit and gave it the experimental name 'K2008-J-224'.

In August 2007, line 'K2008-J-224' was vegetatively propagated to produce rooted cuttings and plants of the selection were cultivated and evaluated in an open field. In December 2007, line 'K2008-J-224' was observed to have its distinct characteristics remain stable. In February 2008, line 'K2008-J-224' was propagated again and plants were cultivated. In May 2008, the distinct characteristics of line 'K2008-J-224' were confirmed to be fixed and stable. Line 'K2008-J-224' was later named 'SAKPXC011' and was found to reproduce true to type in successive generations of asexual propagation via vegetative propagation.

SUMMARY

The following are the most outstanding and distinguishing characteristics of this new variety when grown under normal horticultural practices in Salinas, Calif.

1. Purplish-rose flower color; and
2. Semi-creeping growth habit.

DESCRIPTION OF THE PHOTOGRAPHS

This new *Petunia-Calibrachoa* plant is illustrated by the accompanying photographs which show the plant's overall plant habit including form, foliage, and flowers. The photographs are of a three-month-old plant grown in Salinas, Calif. under greenhouse conditions in the spring of 2012. The colors shown are as true as can be reasonably obtained by conventional photographic procedures.

DESCRIPTION OF THE NEW VARIETY

Figure 1:
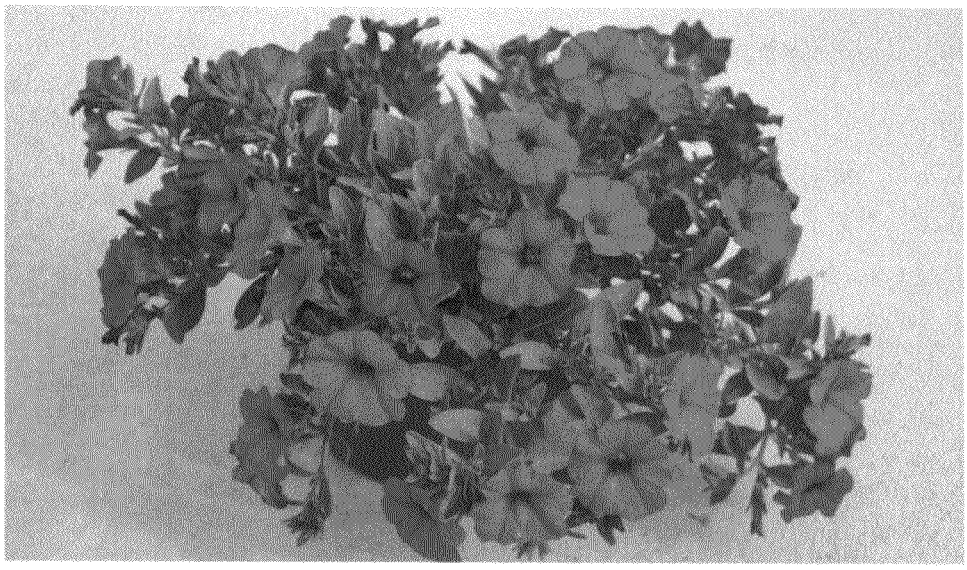
FIG. 1 shows the overall plant habit of the plant grown in a pot.
Figure 2:
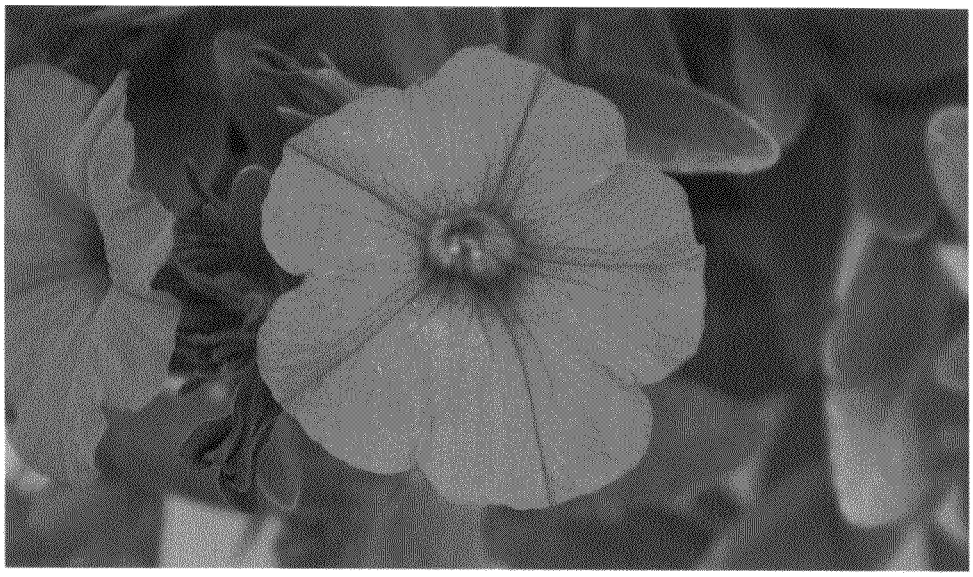
FIG. 2 shows the mature inflorescence of the plant.

The following detailed descriptions set forth the distinctive characteristics of 'SAKPXC011'. The data which define these characteristics were collected from asexual reproductions carried out in Salinas, Calif. Data was collected on three-month-old plants grown under greenhouse conditions in Salinas, Calif. in the summer of 2012. Color references are to The R.H.S. Colour Chart of The Royal Horticultural Society of London (R.H.S.), $4^{th}$ edition.

Classification:
*Family.*—Solanaceae.
*Botanical.*—*Petunia-Calibrachoa* intergeneric hybrid.
*Common.*—Petchoa.
*Designation.*—'SAKPXC011'.

Parentage:
*Female parent.*—Proprietary hybrid *petunia* plant line 'AM6-106A' (unpatented).
*Male parent.*—Proprietary hybrid *calibrachoa* plant line 'SAKCAL093' (U.S. Plant Pat. No. 20,490).

Growth:
*Time to produce a rooted cutting.*—4 weeks.
*Environmental conditions for plant growth.*—The terminal 1.0 to 1.5 inches of an actively growing stem was excised. The vegetative cuttings were propagated in four weeks. The base of the cuttings were dipped for 1 to 2 seconds in a 1:9 solution of Dip 'N Grow (1 solution:9 water) root inducing solution immediately prior to sticking into the cell trays. Cuttings were stuck into plastic cell trays having 98 cells, and containing a moistened peat moss-based growing medium. For the first week, the cuttings were misted with water from overhead for 20 seconds, one time per hour. For the second week, the cuttings were misted one time every 2 hours for 10 seconds. After that time, the cuttings were misted occasionally until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.
*Time to bloom from propagation.*—8 to 10 weeks.

Plant description:
*Habit.*—Semi-creeping.
*Life cycle.*—Tender perennial.
*Form.*—Decumbant, branching.
*Height* (*from soil line to top of foliage*).—14.0 cm.
*Spread.*—48.0 cm.

Stems:
*General.*—Circular in cross-section.
*Stem length.*—1.0 cm from soil line to first node, 10.0 cm to 11.0 cm total.
*Diameter.*—0.2 cm.
*Internode length.*—2.0 cm to 2.5 cm.
*Color.*—RHS 144A (Yellow-Green).
*Pubescence.*—Heavy Color: RHS N155A (White).
*Anthocyanin color.*—Slight, only on peduncle, color is RHS N187A (Greyed-Purple).

Leaves:
*Arrangement.*—Alternate.
*Shape.*—Elliptic.
*Apex.*—Obtuse.
*Base.*—Attenuate.
*Margin.*—Entire.
*Venation.*—Pinnate.
*Surface appearance* (*both surfaces*).—Dull.
*Surface pubescence* (*both surfaces*).—Light.
*Surface pubescence color* (*both surfaces*).—RHS N155A (White).
*Length.*—5.0 cm.
*Width.*—2.0 cm.
*Color.*—Upper surface: RHS 147A (Yellow-Green). Lower surface: RHS 147B (Yellow-Green).
*Fragrance.*—Absent.

Flowers:
*Total number of flowers.*—Approximately 50.
*Flowering habit.*—Indeterminate.
*Flower type.*—Solitary.
*Flowering requirements.*—Will flower so long as day length is greater than 12 hours and temperature exceeds 13° C.
*Duration of flowers.*—5 days.
*Shape.*—The flowers are funnel shaped with five fissures and a shallow, yet slight, indentation of the petal tip at the midvein.
*Fragrance.*—Absent.

Flower buds:
*Surface texture.*—Pubescent.
*Length.*—3.5 cm.
*Diameter.*—2.0 cm.
*Shape.*—Ovate.
*Color.*—RHS 72A (Red-Purple).

Peduncle:
*Length.*—2.0 cm.
*Diameter.*—0.1 cm.
*Color.*—RHS 144A (Yellow-Green).
*Texture.*—Dull, light pubescence, pubescence color is RHS N155A (White).

Flower description:
*Flower depth.*—1.0 cm.
*Flower tube length.*—3.0 cm.
*Flower tube diameter.*—0.8 cm.
*Flower diameter.*—5.0 cm.

Calyx:
*Arrangement.*—Composed of 5 sepals, fused below the middle.
*Sepals.*—Shape: Elliptical. Apex: Obtuse. Margin: Entire. Length: 1.5 cm. Diameter: 0.25 cm. Color: Upper surface: RHS 137A (Green). Lower surface: RHS 137A (Green).

Corolla:
*Arrangement.*—Composed of 5 petals, fused.
*Diameter.*—4.0 cm.
*Petal.*—Apex: Truncate. Margin: Entire. Base: Fused. Pubescence: Glabrous. Lobe length: 2.0 cm. Lobe width: 2.5 cm. Color: Lobe color: Upper surface: Closest to but darker and brighter than RHS N74A (Red-Purple). Lower surface: RHS 72A (Red-Purple).
*Corolla tube color.*—Inner: RHS 13A (Yellow) with RHS 187A (Greyed-Purple). Outer: RHS 1C (Green-Yellow) with RHS N144D (Yellow-Green) veins.

Reproductive organs:
*Stamen number.*—5, free.
*Stamen color.*—Anther color: RHS 13C (Yellow). Filament color: RHS 2C (Yellow).
*Pollen color.*—RHS 11A (Yellow).
*Pollen amount.*—Abundant.
*Ovary.*—Superior.
*Placenta arrangement.*—Central.
*Pistil number.*—1 per inflorescence.
*Pistil length.*—1.2 cm.
*Stigma color.*—RHS 144A (Yellow-Green).
*Style length.*—1.0 cm.
*Style color.*—RHS 144C (Yellow-Green).

*Seed production.*—Absent.

Disease and insect resistance: Excellent resistance to rain, heat and drought. Temperature below 10° C. is not optimal. Plants are susceptible to *Botrytis*, powdery mildew, various stem and root rots, and certain viruses, like Tobacco Mosaic Virus and *Impatiens* Necrotic Spotted Virus. Plants can be infested with aphids, leafminer, whitefly and various *Lepitopdera.*

COMPARISON WITH PARENTAL LINES AND KNOWN VARIETY

'SAKPXC011' is a new and unique variety of intergeneric *Petunia Calibrachoa* owing to its purplish-rose flower color and semi-creeping plant growth habit. 'SAKPXC011' is distinguished from its parents mainly by flower color and plant growth habit as shown in Table 1 below):

TABLE 1

Comparison with Parental Lines

| Characteristic | 'SAKPXC011' | Male Parent 'SAKCAL093' | Female Parent 'AM6-106A' |
|---|---|---|---|
| Flower color | Purplish-rose | Burgundy | Rose |
| Plant growth habit | Semi-creeping | Creeping | Mounding |

'SAKPXC011' is a new and unique variety of intergeneric *Petunia-Calibrachoa* owing to its purplish-rose flower color and semi-creeping plant growth habit. 'SAKPXC011' is most similar to the commercial *Petunia-Calibrachoa* variety 'Kakegawa S89' (U.S. Plant Pat. No. 19,130), commercially known as SuperCal® 'Neon Rose'; however there are differences in the flower color as described in the table below (color references are to The Royal Horticultural Society Colour Chart, 4th edition):

TABLE 2

Comparison with Similar Variety

| Characteristic | 'SAKPXC011' | 'Kakegawa S89' |
|---|---|---|
| Petal color, upper surface | Closest to but darker and brighter than RHS N74A (Red-Purple) | RHS N66A (Red-Purple) with RHS 64A (Red-Purple) veins |
| Petal color, lower surface | RHS 72A (Red-Purple) | RHS N66C (Red-Purple) with RHS 142A (Green) veins |
| Plant growth habit | Semi-creeping | Mounding |

We claim:

1. A new and distinct cultivar of *Petunia-Calibrachoa* hybrid plant as shown and described herein.

* * * * *